(12) United States Patent
Takanashi et al.

(10) Patent No.: US 6,553,091 B2
(45) Date of Patent: Apr. 22, 2003

(54) X-RAY CT APPARATUS

(75) Inventors: Tetsuyuki Takanashi, Yaita (JP); Tomiya Sasaki, Nasu-gun (JP); Yuichi Kasuya, Nasu-gun (JP); Masahiro Kuroda, Yokohama (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/885,115

(22) Filed: Jun. 21, 2001

(65) Prior Publication Data
US 2001/0055362 A1 Dec. 27, 2001

(30) Foreign Application Priority Data
Jun. 22, 2000 (JP) .......................... 2000-187874

(51) Int. Cl.⁷ .............................................. G01N 23/00
(52) U.S. Cl. ............................ 378/15; 378/207; 378/94
(58) Field of Search .............................. 378/4, 15, 114, 378/205, 207, 94

(56) References Cited

U.S. PATENT DOCUMENTS

| | | | | |
|---|---|---|---|---|
| 4,560,870 A | | 12/1985 | Ramamurti | |
| 4,894,778 A | * | 1/1990 | Matsumura | 378/15 |
| 4,916,718 A | * | 4/1990 | Manring | 378/15 |
| 5,229,871 A | * | 7/1993 | Czarnek et al. | 359/109 |
| 5,469,488 A | * | 11/1995 | Ono | 250/551 |

* cited by examiner

Primary Examiner—Robert H. Kim
Assistant Examiner—Hoon K. Song
(74) Attorney, Agent, or Firm—Oblon, Spivak, McClelland, Maier & Neustadt, P.C.

(57) ABSTRACT

An X-ray CT apparatus includes a pair of an involute gear and a magnetic sensor as a structure for detecting the rotation of the gantry rotary section in a non-contact fashion. The involute gear imparts a periodic change in the magnetic flux in the circumferential direction of a circle coaxial with the gantry rotary section. The magnetic sensor including the magnet and the magnetic reluctance (MR) elements detects the change in the magnetic flux caused by the rotation of the involute gear together with the gantry rotary section to generate a pulse signal conforming with the change in the magnetic flux. The pulse signal obtained from the magnetic sensor is supplied to the servo amplifier, the CT main control section, etc. via the signal processing unit.

20 Claims, 10 Drawing Sheets

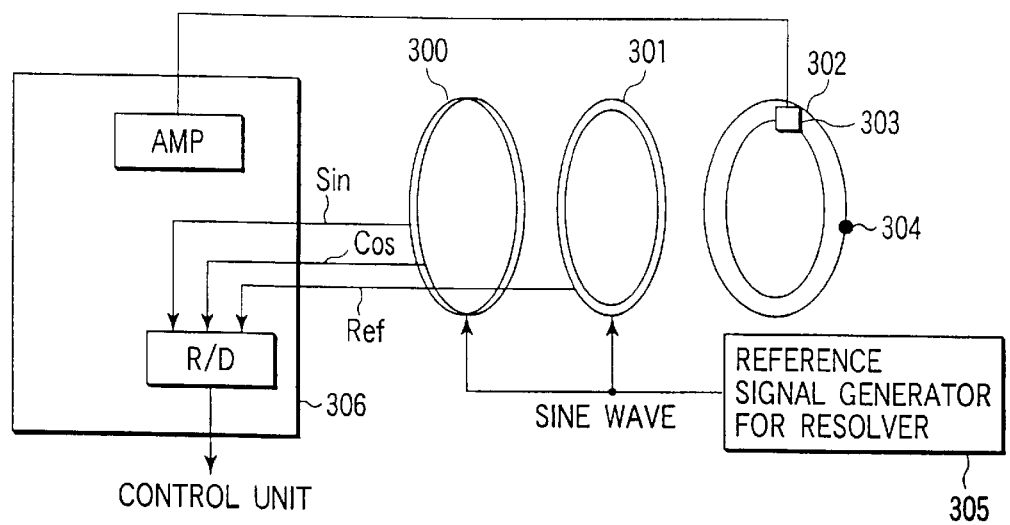
FIG. 1 PRIOR ART
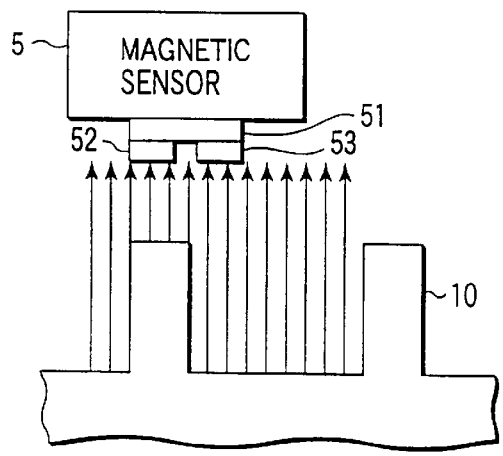
FIG. 3A
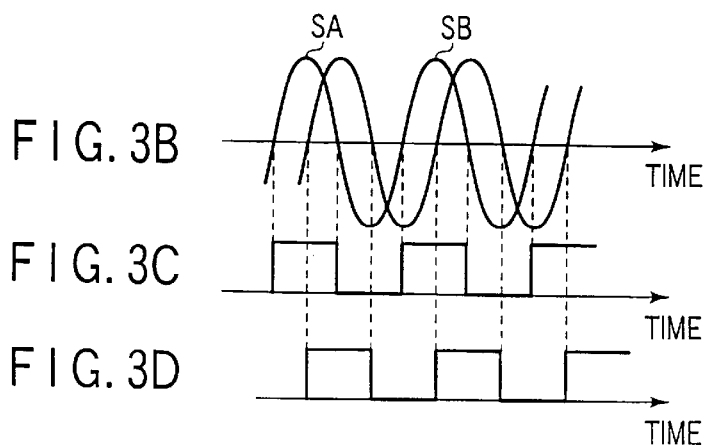
FIG. 3B
FIG. 3C
FIG. 3D

X-RAY CT APPARATUS

CROSS-REFERENCE TO RELATED APPLICATIONS

This application is based upon and claims the benefit of priority from the prior Japanese Patent Application No. 2000-187874, filed Jun. 22, 2000, the entire contents of which are incorporated herein by reference.

BACKGROUND OF THE INVENTION

The present invention relates to an X-ray CT (computed tomography) apparatus, particularly, to a mechanism for detecting the rotation of a rotary section of a gantry included in the X-ray CT (computed tomography) apparatus and to the control of the detecting mechanism.

In recent years, the function of the X-ray CT apparatus has been enhanced and diversified. One of the diversifications of the function is small sound imaging, i.e., the situation in which mechanical vibration is suppressed as much as possible so as to photograph a patient to be examined in a quiet operating environment. In a system in which the rotary driving force generated from a motor arranged in the stationary section of the gantry is transmitted via a gear, a belt, etc. so as to drive the rotary section, a big operating sound (noise) is generated by, for example, the sliding of the belt so as to produce anxiety or unpleasantness in the patient or the X-ray engineer. In these circumstances, the sound suppressing technology is applied to the rotary driving mechanism of the X-ray CT apparatus in order to prevent such a noise.

One of the technologies that has appeared in accordance with the trend toward small sound imaging is an X-ray CT apparatus in which a direct drive (DD) motor driving system is applied to the rotary mechanism of the gantry. In the direct drive motor driving system, a large number of magnets are mounted to the rotary section of the gantry. At the same time, a winding is mounted to the stationary section of the gantry. By supplying an electric current to the winding, the rotary section of the gantry is directly rotated as a rotor of the motor. The mechanism for transmitting the rotating force such as a belt and a gear is not included in the direct drive motor driving system, making it possible to suppress the sound.

A resolver mechanism is mounted to the X-ray CT apparatus employing such a direct drive motor driving system in order to detect the rotation of the rotary section of the gantry and to control the rotating position and the rotation speed.

FIG. 1 schematically shows the conventional resolver mechanism. As shown in FIG. 1, a resolver 300, a transformer 301, and a direct drive (DD) motor 302 are mounted to the gantry rotary section and the gantry stationary section included in the X-ray CT apparatus. These members are mounted to the structure on the side of the gantry rotary section and to the structure on the side of the gantry stationary section. For example, the primary winding of the transformer 301 and the secondary winding corresponding to the resolver are mounted to the gantry rotary section and the gantry stationary section.

The resolver 300 applied to the X-ray CT apparatus, which is used for detecting the rotating position of the gantry rotary section and for detecting the rotating speed or rate, is shaped like a ring having a relatively large diameter and conforming with the shape of the gantry rotary section. A reference signal consisting of a Sin wave is generated from a reference signal generator 305 for the resolver, which is mounted in the rotary section of the gantry, so as to be supplied to the resolver 300. Upon receipt of the reference signal, the resolver 300 generates a sin signal and cos signal, and these signals are supplied to a controller 306 mounted in the stationary section of the gantry. These sin signal, cos signal and the reference signal generated from the reference signal generator 305 through the transformer 301 are converted into a digital signal by an R/D circuit (reference/detection signal processing circuit) so as to form the basic pulse. The frequency of the digital signal is divided so as to be utilized for detecting the position of the rotary section. To be more specific, the basic pulse is supplied to the control section of the X-ray CT apparatus so as to be utilized for various control operations based on, for example, the detection of the rotary position and the detection of the rotating speed, thereby controlling the explosion of the X-ray, the data collection and the trigger of an X-ray tube.

The rotary detection mechanism utilizing the resolver described above gives rise to problems as described below.

First of all, the resolver is a structure having a large diameter. For the mass production of the resolver, large scale automation facilities are required, leading to a high manufacturing cost of the X-ray CT apparatus. Also, in the conventional gantry rotary section having the resolver mechanism incorporated therein, a large resolver structure, etc. is arranged behind a data transfer unit for transmitting data by optical communication utilizing an LED or a photo diode between the gantry stationary section and the rotary section. As a result, it is difficult to gain access to the resolver mechanism in performing, for example, a maintenance operation, giving rise to the problem that much labor is required for the inspection, the renewal operation, etc. It should also be noted that a signal transmitting line is drawn directly from the coil of the resolver mechanism in order to take out signals from the coil of the resolver mechanism. What should be noted is that, in the event of, for example, wire breakage, it is difficult to cope with the wire breakage problem flexibly, with the result that it is unavoidable to renew the entire resolver.

An additional problem to be noted is that the resolver is incapable of executing the function of detecting the rotation unless the reference signal generator for generating the reference signal is mounted to the stationary section of the gantry as described above so as to supply power to the entire rotary section and stationary section of the gantry via a slip ring. This particular construction is undesirable in terms of efficiency and safety in the maintenance step. Under these circumstances, vigorous efforts are being made in an attempt to develop a new improvement capable of overcoming the problems inherent in the mechanism for detecting the rotation by a resolver.

BRIEF SUMMARY OF THE INVENTION

An object of the present invention is to provide an X-ray CT apparatus simple in construction, permitting the maintenance operation at a low cost, and capable of detecting rotation and controlling the rotation with a high accuracy.

According to a first aspect of the present invention, there is provided an X-ray CT apparatus, comprising:
  a gantry including a substantially cylindrical rotary section and a stationary section rotatably holding the rotary section;
  rotation detecting means for detecting the rotation of the rotary section to generate a rotation detecting signal;
  correcting means for correcting the rotation detecting signal; and calculating means for calculating at least one of the rotating position and the rotating speed of the rotary section on the basis of the corrected detecting signal from the correcting means.

According to a second aspect of the present invention, there is provided an X-ray CT apparatus, comprising:

a gantry including a substantially cylindrical rotary section and a stationary section rotatably holding the rotary section;

rotation detecting means for detecting the rotation of the rotary section to generate a rotation detecting signal, the rotation detecting means including a target section to be detected, which is mounted to one of the rotary section and the stationary section to impart a periodic change in the magnetic flux in the rotating direction of the rotary section, and a rotation detecting sensor mounted to the other of the rotary section and the stationary section with a gap provided between the target section to detect the change in the magnetic flux generated in the target section in accordance with rotation of the rotary section and to generate a rotation detecting signal in accordance with detection of the change in the magnetic flux;

a sensor for detecting a reference position of the rotary section to generate a reference position detecting signal;

calculating means for calculating at least one of the rotating position and the rotating speed of the rotary section on the basis of the detection signal, the calculating means calculating the rotating position of the rotary section on the basis of the reference position signal generated from a position sensor and the rotating speed of the rotary section and also calculating a correction amount conforming with the position from the rotation detecting signal; and moving means for slightly moving the rotation detecting sensor relative to the target section in accordance with the correcting amount to maintain constant the gap between the target section and the rotation detecting sensor.

Further, according to a third aspect of the present invention, there is provided an X-ray CT apparatus, comprising:

a gantry including a substantially cylindrical rotary section and a stationary section rotatably holding the rotary section;

rotation detecting means for detecting the rotation of the rotary section to generate a rotation detecting signal, the rotation detecting means including a ring-like target section to be detected, which is mounted to any one of the rotary section and the stationary section and having a periodic slit pattern formed therein, and an optical sensor mounted to the other of the rotary section and the stationary section in a manner to face the target section to detect the light ray passing through the slit pattern of the target section in accordance with rotation of the rotary section and, thus, to generate a detection signal;

correcting means for correcting the rotation detecting signal; and calculating means for calculating at least one of the rotating position and the rotating speed of the rotary section on the basis of a corrected detecting signal from the correcting means.

Yet further, according to a fourth aspect of the present invention, there is provided an X-ray CT apparatus, comprising:

a gantry including a substantially cylindrical rotary section and a stationary section rotatably holding the rotary section;

detectable section, mounted on one of the rotary section and the stationary section, for applying a periodical change on a magnetic flux generated in a circumferential space which is coaxially defined around the rotary section;

detecting means, mounted on the another of the rotary section and the stationary section, for detecting the change of the magnetic flux which is produced due to the rotation of the rotary section, to generate a rotation detecting signal; and calculating means for calculating at least one of the rotating position and the rotating speed of the rotary section on the basis of the detecting signal from the detecting means.

Furthermore, according to a fourth aspect of the present invention, there is provided an X-ray CT apparatus, comprising:

a gantry including a substantially cylindrical rotary section and a stationary section rotatably holding the rotary section;

motor for directly driving the rotary section to rotate the rotary section;

ring-shaped detectable section mounted on one of the rotary section and the stationary section and having a plurality of slits periodically arranged on the section;

detecting means, mounted on the another of the rotary section and the stationary section, for detecting light rays passing through the slit to generate a rotation detecting signal; and means for generating an encoded signal based on the rotation detection signal from the detecting means.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently embodiments of the invention, and together with the general description given above and the detailed description of the embodiments given below, serve to explain the principles of the invention.

FIG. 1 is a block diagram schematically showing the conventional resolver mechanism and its peripheral circuit;

FIG. 3A is a block diagram schematically showing the combination of the magnetic sensor shown in FIG. 2 and an involute gear;

FIG. 3B shows the wave form denoting the detection signal generated from the magnetic sensor shown in FIG. 3A;

FIGS. 3C and 3D show the wave forms of the pulses generated by processing the detection signals shown in FIG. 3B;

DETAILED DESCRIPTION OF THE INVENTION

X-ray CT apparatuses according to some embodiments of the present invention will now be described with reference to the accompanying drawings.

Figure 2:
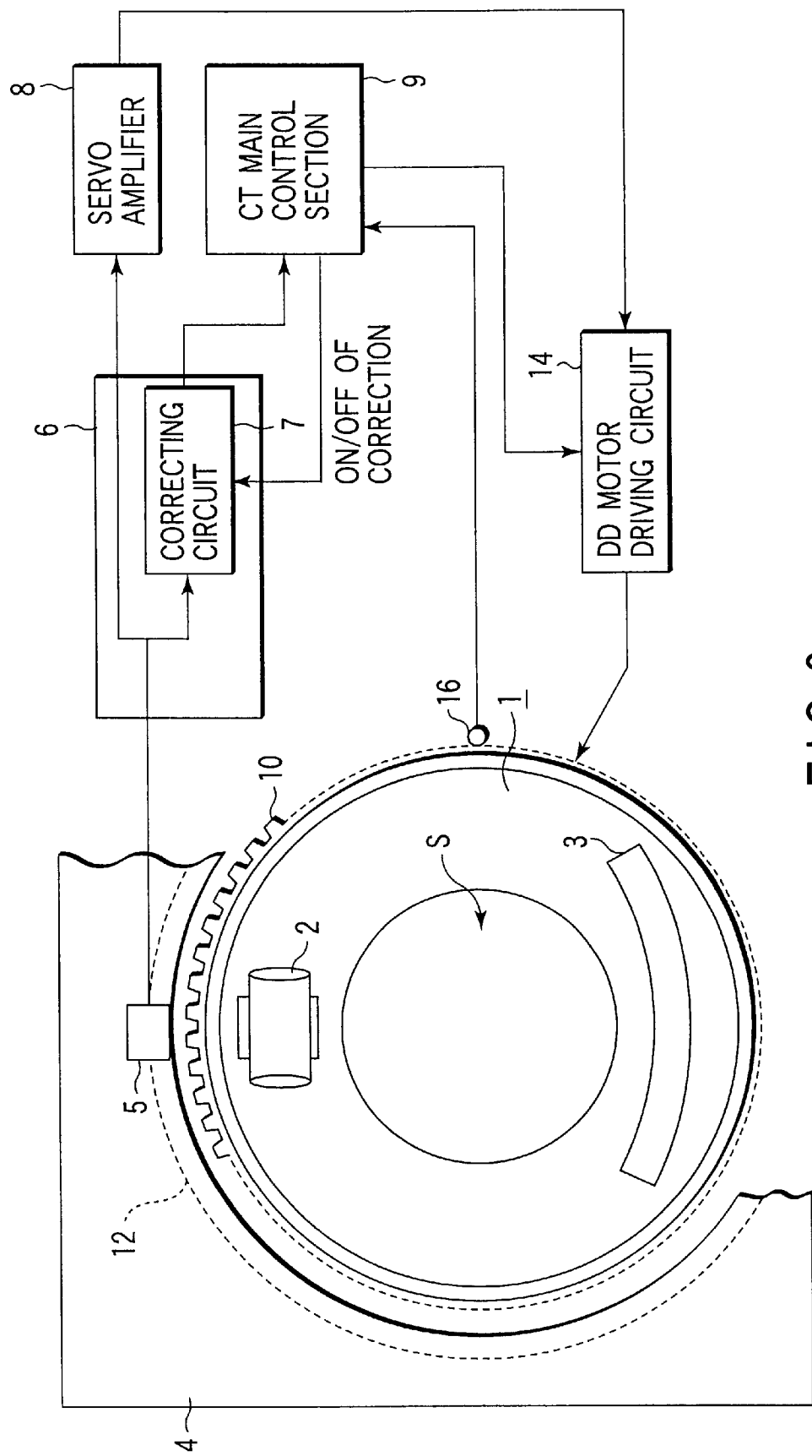
FIG. 2 is a block diagram schematically showing an X-ray CT apparatus according to a first embodiment of the present invention.

FIG. 2 schematically shows the construction of an X-ray CT apparatus according to a first embodiment of the present invention.

A reference numeral 1 shown in FIG. 2 denotes a substantially cylindrical rotary section of a gantry, and a reference numeral 4 denotes a stationary section of the gantry. An X-ray tube 2 for emitting an X-ray to a patient to be examined and an X-ray detector 3 for detecting the X-ray passing through the patient are mounted to the rotary section 1 of the gantry to face each other with a cylindrical space S, into which the to-be-examined body or object such as patient or article is inserted, provided therebetween. Also, a mounting unit housing a circuit board of a signal processing circuit (not shown) for processing the detection signal generated from the detector 3 is mounted to the rotary section of the gantry. The gantry rotary section 1 of the particular construction is rotatably supported by the gantry stationary section 4 with a bearing provided therebetween.

In the system in which the rotary driving force generated from a motor mounted to the stationary section of the gantry is transmitted through a gear, a belt, etc. so as to drive the rotary section of the gantry, a big operating noise based on, for example, the sliding of the belt, i.e., a mechanical noise, is generated so as to impart an anxiety or unpleasantness to the patient and the X-ray engineer. In order to suppress the noise, a rotation driving mechanism to which is applied a noise suppressing technology described below is incorporated in the X-ray CT apparatus widely used nowadays.

Employed in the X-ray CT apparatus according to the first embodiment of the present invention is a direct drive (DD) motor driving system as a low noise type rotation driving system. To be more specific, a winding 11 is mounted to the gantry rotary section 1, and a magnet 12 is mounted to the gantry stationary section 4. If an electric current is supplied to the winding 11, the magnetic flux generated from the magnet 12 and the magnetic flux generated from the winding 11 are repelled each other, with the result that the gantry rotary section 1 is directly rotated in a non-contact fashion as a rotor of the motor. In the present invention, a direct drive (DD) motor driving system is employed in this embodiment as a low noise type rotation driving system. However, in the X-ray CT apparatus of the present invention, the driving system is not limited to the direct drive (DD) motor driving system. As apparent from the entire description of this specification, the driving system is not limited to a particular rotation driving system.

In the X-ray CT apparatus according to the first embodiment of the present invention, employed is the mechanism for detecting the rotation of the gantry rotary section 1 in a non-contact fashion as described below. Specifically, an involute gear 10 is mounted as an object of detection of the rotation on the cylinder outer circumferential surface of the gantry rotary section 1 facing the stationary section 4, as shown in FIG. 2. The involute gear 10 is rotated in the circumferential direction of a circle coaxial with the gantry rotary section 1, and a periodic change in the flux is generated in the gap between the stationary section 4 and the rotary section 1 in accordance with rotation of the involute gear 10. The involute gear 10 is advantageous in that the gear 10 can be manufactured easily with a low cost and that the processing accuracy is high. Incidentally, it is possible to apply, for example, a skiving treatment to the magnetic portion of the gantry rotary section 1 so as to have the involute gear 10 formed integrally with the magnetic portion.

On the other hand, a magnetic sensor 5 is mounted to the gantry stationary section 4 so as to be positioned close to the involute gear 10 of the gantry rotary section 1. The gap between the magnetic sensor 5 and the involute gear 10 is set at a predetermined length, e.g., at about 1 mm. The magnetic sensor 5 generates a detection signal having a wave form dependent on the change in the magnetic flux in accordance with rotation of the involute gear 10 together with the gantry rotary section 1, and the detection signal thus generated is processed so as to output a pulse signal conforming with the detection signal.

The pulse signal obtained by the magnetic sensor 5 is supplied to a servo amplifier 8, a CT main control section 9, etc. via a signal processing unit 6. A switch and a correcting circuit 7 are arranged within the signal processing unit 6. The signal processing unit 6 will be described herein later in detail. The signal from the servo amplifier 8 is supplied to a DC motor driving circuit 14 serving to supply a driving signal to the winding 11 of the DC motor.

The DC motor driving circuit 14 generates a driving signal in accordance with the output from the servo amplifier 8 so as to rotate the rotary section 1 at a rotating speed set by the CT main control section 9. The CT main control section 9 supplies an instruction to start or stop the rotation or an instruction to set the rotary mode including an instruction of the rotating speed to the DD motor driving circuit 14. A reference position sensor 16 is mounted to the stationary section 4 of the gantry. A certain reference position of the rotary section 1 is detected by the sensor 16, and a reference position signal is generated from the sensor 16 so as to be supplied to the CT main control section 9. It follows that, upon receipt of the reference position signal, the CT main control section 9 obtains by the arithmetic calculation the rotating position of the rotary section 1 on the basis of the time from the timing of receiving the reference position signal and the rotating speed of the rotary section 1 so as to generate a position signal. In other words, the servo amplifier 8 receives the pulse signal from the magnetic sensor 5 and controls the direct drive motor based on the pulse signal so as to control the rotation driving of the gantry rotary section 1. The CT main control section 9 also receives the pulse signal from the magnetic sensor 5 so as to calculate the rotating position and the rotating speed of the gantry rotary section 1 based on the pulse signal, thereby controlling the operation of the entire X-ray CT apparatus. Incidentally, in the practical mounting, the CT main control section 9 is said to require a higher accuracy than the servo amplifier 8 relative to the pulse signal generated from the magnetic sensor 5.

The principle of detecting the rotation of the rotary section 1 by the combination of the magnetic sensor and the involute gear will now be described with reference to FIGS. 3A to 3D. As shown in FIG. 3A, a magnet 51 generating a magnetic flux and two magneto-resistance elements 52, 53 are mounted to the magnetic sensor 5. These two magneto-resistance sensors 52, 53 are mounted to that surface of the magnet 51 which faces the rotary section 1. Apparently, it is possible to use an electromagnet including, for example, a coil in place of the magnet 51.

As apparent from FIG. 3A, the concentrating function of the magnetic flux generated from the magnet 51 is changed in the involute gear 10 in accordance with the shape or position of the tooth of the involute gear 10. If the involute gear 10 is rotated together with the gantry rotary section 1, a periodic change in the magnetic flux is generated around the magnetic sensor in accordance with the rotation. The magneto-resistance (MR) elements 52 and 53 exhibit a change in the resistance conforming with the change in the magnetic flux receiving the function by the rotation of the involute gear 10, with the result that an electric signal conforming to the change in the resistance is generated.

FIG. 3B shows a sine wave signal SA (phase A) generated from the magneto-resistance element 52 and a cosine wave signal SB (phase B) obtained by the magneto-resistance element 53. On the other hand, FIG. 3C shows a pulse signal PA that is produced on the basis of the sine wave signal SA of phase A, and FIG. 3D shows a pulse signal PB that is produced on the basis of the cosine wave signal SB of phase B. The pulse signals PA and PB shown in FIGS. 3C and 3D, respectively, are produced in a zero-cross detection circuit (not shown) serving to detect the zero-cross between the sine wave signal SA of phase A and the cosine wave signal SB of phase B so as to rise or fall at the zero-cross point. In the CT main control section 9, the rotating position and the rotating speed are calculated on the basis of the phase difference between the pulse signal SA of phase A and the pulse signal SB of phase B.

In the practical mounting, the number of teeth of the involute gear 10 is set at, for example, 432. In this case, 432 sine wave signals SA of phase A and 432 cosine wave signals SB of phase B are generated and subjected to an A/D conversion and the resultant digital signals are supplied to, for example, a 25 multiplying circuit, with the result that 10800 phase A pulse signals and phase B pulse signals are generated for one complete rotation of the involute gear 10.

In this embodiment of the present invention, some measures given below are take against the distortion of the wave form of the output signals from the magnetic sensor 5 in the circuit construction described above.

In the X-ray CT apparatus, a high accuracy is required for the output signal from the magnetic sensor 5 for performing the position detection and the rotation control of the gantry rotary section 1 with a high accuracy. To be more specific, the error of the pulse signals of phases A and B is required to fall within a predetermined range, e.g., a range of ±3%. If distortion is included in the wave form of the signal before the A/D conversion, the accuracy of the pulse signal multiplied by 25 exceeds the error range of ±15%.

Under the circumstances, first and second optimizing technologies are applied to the shape of the involute gear 10 that is to be detected by the magnetic sensor 5.

Figure 4A:
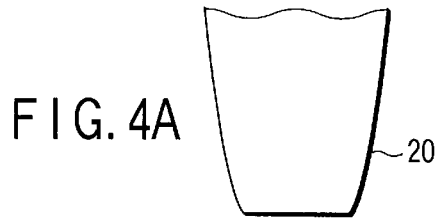
FIG. 4A is a side view schematically showing the shape of a tooth tip of the involute gear before the shape of the involute gear shown in FIG. 2 is made optimum.
Figure 4B:
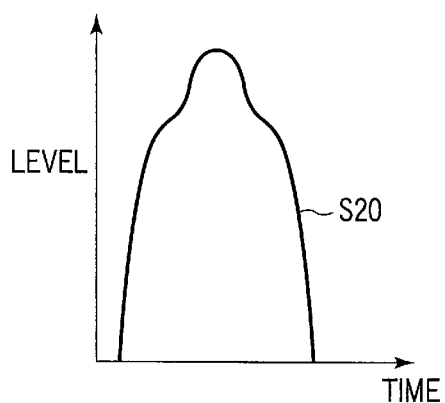
FIG. 4B shows the wave form showing the output signal generated from a magnetic sensor that has detected the change in the magnetic flux receiving function from the tooth tip of the involute gear.

FIGS. 4A, 4B, 5A and 5B are for explaining the first shape optimizing method and show the tooth tip of the involute gear before the shape optimization and after the shape optimization and the wave forms of the output signals from the magnetic sensor 5 that has detected the change in the magnetic flux receiving the function from the tooth tip. Specifically, FIG. 4A shows the shape of the tooth tip of the involute gear before the shape optimization. As shown in the drawing, the edge portion of the tooth tip 20 is made slightly roundish as the shape inherent in the involute gear. Since the involute gear has a roundish tooth tip, the wave form S20 of the output signal is distorted as shown in FIG. 4B.

Figure 5A:
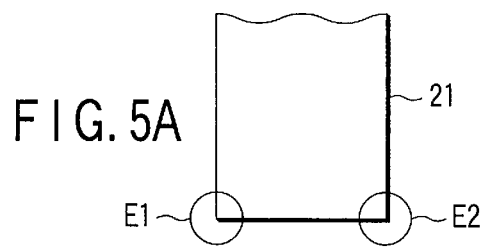
FIG. 5A is a side view schematically showing the shape of a tooth tip of the involute gear after the shape of the involute gear shown in FIG. 2 is made optimum.
Figure 5B:
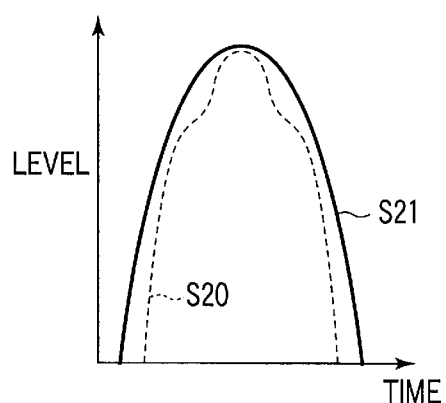
FIG. 5B shows the wave form showing the output signal generated from a magnetic sensor that has detected the change in the magnetic flux receiving function from the tooth tip of the involute gear.

FIG. 5A shows the shape of the tooth tip 21 of the involute gear after the shape optimization. As shown in the drawing, edge portions E1 and E2 of the tooth tip 21 are formed sharp. Since the edge portions E1 and E2 of the tooth tip 21 are formed sharp, the manner of convergence of the magnetic flux is changed, with the result that the distortion of the wave form 21 of the output signal is suppressed so as to exhibit a good wave form as shown in FIG. 5B.

It should be noted that, even if the shape of the involute gear 10 is made optimum, there are cases where a desired accuracy is not achieved. To be more specific, there are cases where the magnetic flux density fails to be rendered uniform because of the shape of the magnet 51 constituting the magnetic sensor 5, the shapes of the magneto-resistance elements 52, 53 and the arrangement of these magnet 51 and the magneto-resistance elements 52, 53, with the result that the wave form of the output signal remains to be distorted.

Under the circumstances, the output signal generated from the magnetic sensor 5 is corrected by the correcting circuit 7 shown in FIG. 2 so as to impart a required accuracy to the output pulse signal.

Figure 6:
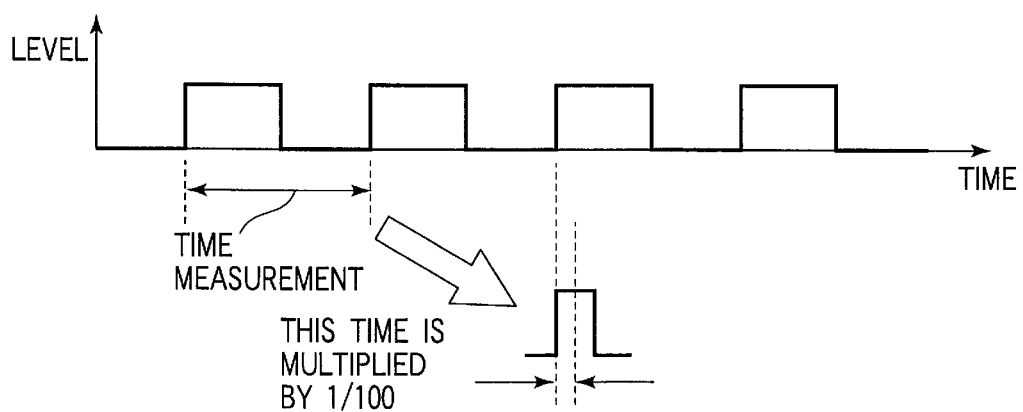
FIG. 6 shows the wave form for explaining an example of the method of correcting the output signal generated from the magnetic sensor shown in FIG. 2.

FIG. 6 shows as an example how to correct the output signal generated from the magnetic sensor 5. An original output signal before the correction, which is generated from the magnetic sensor 5, is supplied to the correcting circuit 7, and the change with time in the magnetic flux is measured based on the output signal in the correcting circuit 7. To be more specific, the time between the adjacent zero-cross points of the wave form of the output signal is counted by utilizing the basic clock pulses. The counted time is less likely to be subjected to the influence by the distortion of the wave form, making it possible to form a count signal of a high accuracy having an error range of ±0.01%.

Then, the measured time, i.e., the count signal, is multiplied by 1/100 so as to form corrected pulse signals each having a pulse length that is ¼ of the 25 multiplied pulse referred to previously, and these corrected pulse signals are successively outputted starting with the pulse after completion of the calculation. In other words, the corrected pulses are outputted at a time interval of 1/100 of the time between the adjacent zero-cross points.

Figure 7:
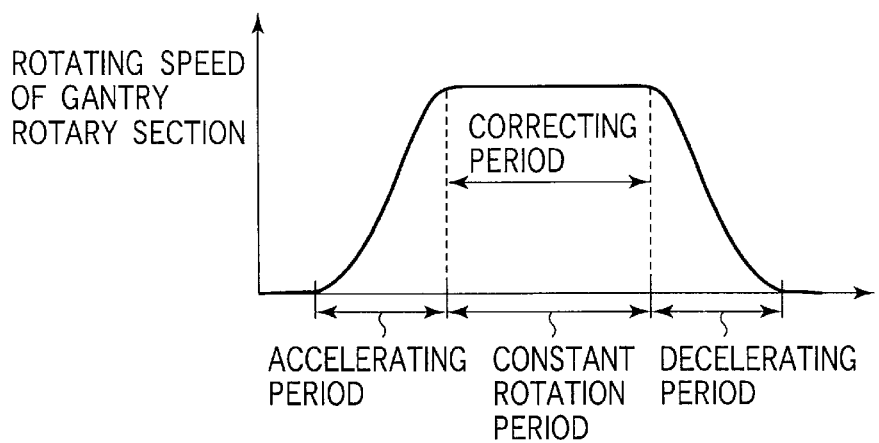
FIG. 7 is a graph showing the correcting period for correcting the output signal generated from the magnetic sensor in the correcting circuit shown in FIG. 2, said correcting period being determined in accordance with the rotating speed of the rotary section of the gantry.

The signal correction in the correcting circuit 7 is performed on the premise of the calculation based on the time measurement. However, it is possible for the calculation for the correction not to be performed because of the restriction in respect of the calculation process capability in the stopping period, the rotation accelerating period and the rotation decelerating period of the gantry rotation section 1, i.e., because of the restriction that it is possible to mount a large scale buffer in the correcting circuit 7. Such being the situation, the correcting operation is performed during the period when the gantry rotary section 1 can be rotated at a constant speed including the maximum speed, excluding the accelerating period or the decelerating period when the rotation of the gantry rotary section 1 is accelerated or decelerated, as shown in FIG. 7. In other words, the CT main control section 9 controls the ON/OFF of the correcting operation performed by the correcting circuit 7 as shown in FIG. 2. By allowing the CT main control section 9 to perform the control of the correcting operation as described above, it is possible to obtain a pulse signal to which the correction is applied only when required.

Incidentally, the original signal to which the correction by the correcting circuit 7 is not applied in respect of the signal supplied to the servo amplifier 8 is supplied to the signal processing unit 6. Also, the original signal, which is not corrected, is supplied to the CT main control section 9 during the rotation accelerating period and the decelerating period of the gantry rotary section 1. This is because a stabilized number of pulse signals are required for the position detection performed by the CT main control section 9.

As described above, according to the first embodiment of the present invention, the mechanism utilizing the magnetic sensor 5 and the involute gear 10 is applied for detecting the rotation of the gantry rotary section 1, making it possible to achieve marked improvements in the miniaturization of the construction, the simplification and the space saving, compared with the conventional resolver system. For example, the resolver mechanism weighs about 80 to 100 kg, whereas the sum of the weights of the magnetic sensor 5 and the gear 10 is only about several kilograms. Also, the manufacturing cost of the rotation detecting mechanism of the present invention is about half the manufacturing cost of the resolver mechanism. If the rotation detecting mechanism of the present invention is miniaturized, the construction of the entire gantry rotary section 1 is rendered simple, leading to improvements in the assembling capability, the maintenance capability and the safety.

In the conventional gantry rotary section to which the resolver mechanism is applied, a large resolver structure, etc. are arranged behind the data transmitting unit for achieving the data transmission between the gantry stationary section and the rotary section by the optical communication utilizing an LED or a photodiode. As a result, it is difficult to gain access to the resolver mechanism in performing, for example, the maintenance operation, giving rise to the problem that a much labor is required for the inspection, the renewal operation, etc. In the rotation detecting mechanism according to the first embodiment of the present invention, however, it is possible to gain access easily to the magnetic sensor 5 or the involute gear 10, making it possible to achieve, for example, the renewal operation in the site of the installation. It is also possible to inspect the function relating to the rotation mechanism of the gantry rotary section 1 by simply supplying an electric current to the motor system and the gantry stationary section 4 without supplying an electric current to the gantry rotary section 1 so as to contribute to the improvement in the maintenance efficiency.

It should also be noted that the rotation detecting mechanism according to the first embodiment of the present invention makes it possible to resolve the problem of the accuracy generated by applying the conventional magnetic sensor.

What should also be noted is that the shape of the involute gear 10 is made optimum so as to stabilize the output pulse signal generated from the magnetic sensor 5 formed of the magneto-resistance elements 52, 53, etc. Also, the pulse signal generated from the magnetic sensor 5 is corrected by the correcting circuit 7. It follows that it is possible to realize a high accuracy required in an X-ray CT apparatus.

To be more specific, it is possible to improve the pulse accuracy, with the voltage fluctuation between 4.0 V and 6.0 V and the gap fluctuation of 1.5 mm to 0.5 mm between the gear and the magnetic sensor taken into account, from the conventional value of ±1 to 2% to ±0.0093%.

As described above, according to the first embodiment of the present invention, it is possible to provide an X-ray CT apparatus simple in construction, high in its maintenance capability, and capable of achieving the rotation detection and the rotation control with a high accuracy.

MODIFICATION OF FIRST EMBODIMENT

It is possible to reverse the arrangement of the magnetic sensor 5 and the involute gear 10 on the premise that the detection signal generated from the magnetic sensor 5 is transmitted appropriately between the gantry rotary section 1 that is rotated continuously and the stationary section 4. To be more specific, it is possible to mount the magnetic sensor 5 in the gantry rotary section 1 and to mount the involute gear 10 to the gantry stationary section 4.

It is also possible to use another gear such as a spur gear in place of the involute gear 10. In this case, it is desirable to change appropriately the shape optimization of the involute gear 10 described above in accordance with the shape and the characteristics of the gear. In short, it suffices to suppress the distortion in the wave form of the output signal caused by the shape or arrangement of the gear itself serving to impart a change in the magnetic flux in the vicinity of the magnetic sensor.

Needless to say, it is possible to apply the technical idea of the present invention to the X-ray CT apparatus in which the driving mechanism of the gantry rotary section differs from the direct drive (DD) driving system, e.g., an X-ray CT apparatus equipped with a mechanism for driving the gantry rotary section by transmitting the rotary driving force generated from a motor via a gear, a belt, etc. In this case, the rotation detection is of non-contact type, making it possible to obtain the prominent effect of the present invention described above, though the noise suppressing effect is somewhat lowered.

SECOND EMBODIMENT

In the second embodiment of the present invention, the pulse accuracy is improved by controlling the movement of the magnetic sensor toward or away from the rotary section 1. The second embodiment can be combined with the first embodiment described previously or can be worked independently.

Figure 8:
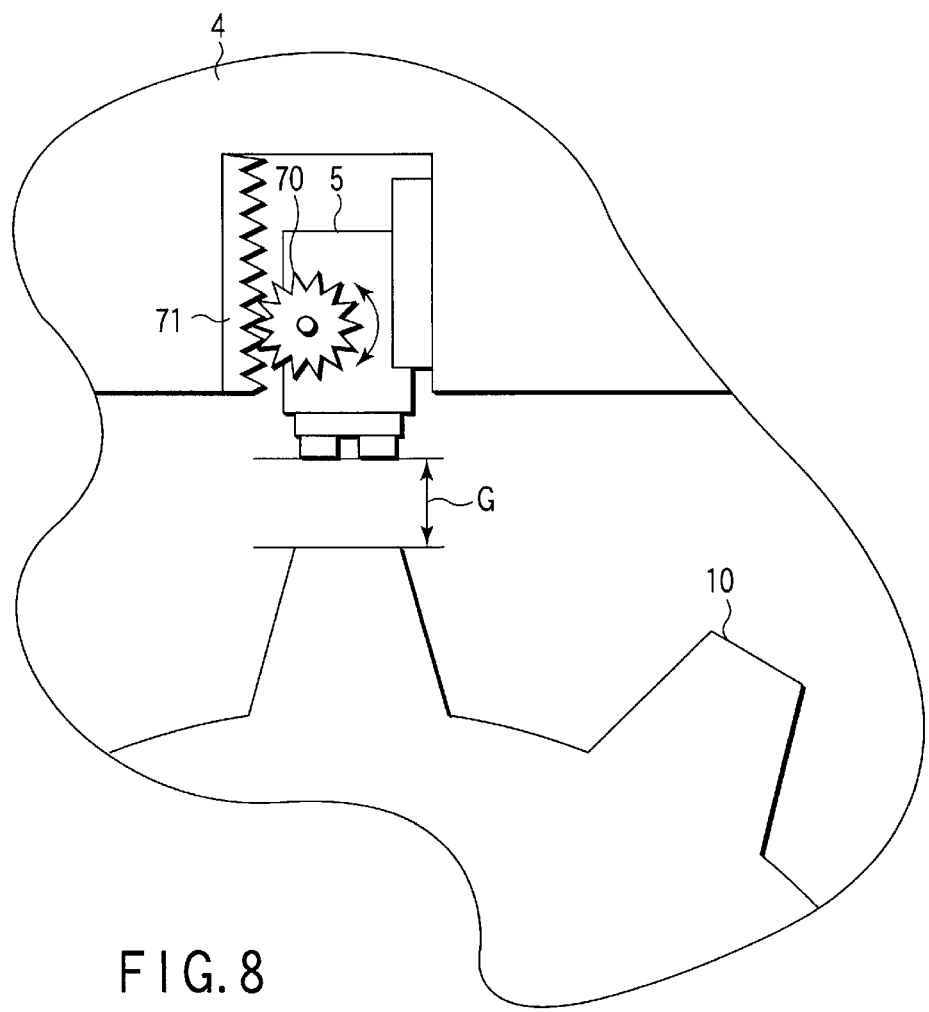
FIG. 8 is a side view, partly broken away, schematically showing the mechanism for realizing the control to permit the magnetic sensor, which can be mounted in the X-ray CT apparatus shown in FIG. 2, to be moved toward or away from the involute gear.

FIG. 8 shows an embodiment in which a control mechanism for controlling the movement of the sensor 5 shown in FIG. 2 toward and away from the stationary section 4 is mounted to the stationary section 4. The particular control mechanism permits the magnetic sensor 5 to be moved toward or away from the involute gear 10 so as to increase or decrease the gap between the involute gear 10 and the magnetic sensor 5. As shown in FIG. 8 as an example, it is possible for the magnetic sensor 5 to be mounted to the gantry stationary section 4 such that the magnetic sensor 5 is slidable toward the involute gear 10. It is also possible for a pinion gear 70 to be mounted to the magnetic sensor 5 and for a rack 71 meshing with the pinion gear 70 to be mounted to the gantry stationary section 4. It is possible to adjust the position of the magnetic sensor 5 by moving the magnetic sensor 5 toward or away from the involute gear 10 by the rotation of the pinion gear 70.

In the case of employing the mechanism in which the involute gear 10 is mounted to the gantry rotary section 1 of the X-ray CT apparatus and the rotation of the involute gear 10 is detected by the magnetic sensor 5 as in the first embodiment of the present invention, the involute gear 10 is rendered relatively large in its diameter. As a result, it is difficult in some cases to manufacture the involute gear 10 as an ideal part close to the correct circle.

If there is a distortion, a recess, a warping, etc. in the shape of the involute gear 10, the gap between the magnetic sensor 5 and the involute gear 10 is changed, with the result that the accuracy of the detection signal generated from the sensor 5 is affected by the shape of the gear 10. This is also the case with the mounting accuracy to the gantry rotary section 1 as well as the processing accuracy of the involute gear 10.

In the second embodiment of the present invention, the magnetic sensor 5 is controlled to be moved toward or away from the involute gear 10 so as to maintain constant the gap between the involute gear 10 and the magnetic sensor 5. In order to obtain the control amount for the particular control, the gantry rotary section 1 is rotated preliminarily and the control amount is determined by the rotating operation. To be more specific, the gantry rotary section 1 is rotated to make at least one complete rotation, and a pulse signal for at least one complete rotation of the rotary section 1 is generated from the magnetic sensor 5 so as to calculate the pulse accuracy for every rotating angle (position) from the pulse signal thus generated. For example, where a recess is generated in a part of the involute gear 10, the pulse signal generated from the magnetic sensor 5, which corresponds to the recessed portion, is fluctuated depending on the recess, i.e., the defect, and the defect data on the recessed portion is obtained as the control amount by the preliminary rotation, with the result that the defect is recognized in advance. The particular recognizing treatment (measurement of the pulse accuracy) is executed by, for example, the CT main control section 9 so as to be stored as the defect data in the memory of the CT main control section 9.

Then, the control amount for moving the magnetic sensor 5 is calculated on the basis of the defect data obtained by the recognizing treatment, and the mechanism shown in FIG. 8 is operated to move the magnetic sensor 5 toward or away from the involute gear 10 so as to maintain constant the gap between the magnetic sensor 5 and the involute gear 10 for every rotating angle. As a result, it is possible to obtain a pulse signal having a predetermined pulse accuracy on the basis of the detection signal generated from the magnetic sensor.

It is possible to realize a further improvement in accuracy and stabilization by executing the control to move the magnetic sensor 5 toward and away from the involute gear 10 for measuring the pulse accuracy appropriately in accordance with the operating state of the X-ray CT apparatus.

For example, it is desirable for the measurement of the pulse accuracy by the preliminary rotating operation described above and for the control to move the magnetic sensor 5 toward or away from the involute gear 10 to be executed for every rotating speed of the gantry rotary section 1 so as to prepare the control data.

Another example is the application to the scanogram or scanoscope photographing. In the scanogram photographing, the X-ray tube is moved to a desired rotating position and a ceiling plate having a patient disposed thereon is moved while maintaining the rotating position of the X-ray tube. In the scanogram photographing of this type, it is possible for the X-ray tube not to be moved to the predetermined rotating position noted above with a high accuracy because of the nonuniformity of the gap between the involute gear 10 and the magnetic sensor 5. Such being the situation, the preliminary rotating operation described above is performed before the scanogram photographing so as to measure the pulse accuracy by preliminarily rotating the gantry rotary section 1 to make at least one complete rotation, and the control to move the magnetic sensor 5 toward or away from the involute gear 10 is performed, thereby moving the X-ray tube to the rotating position noted above with a high accuracy.

Figure 9:
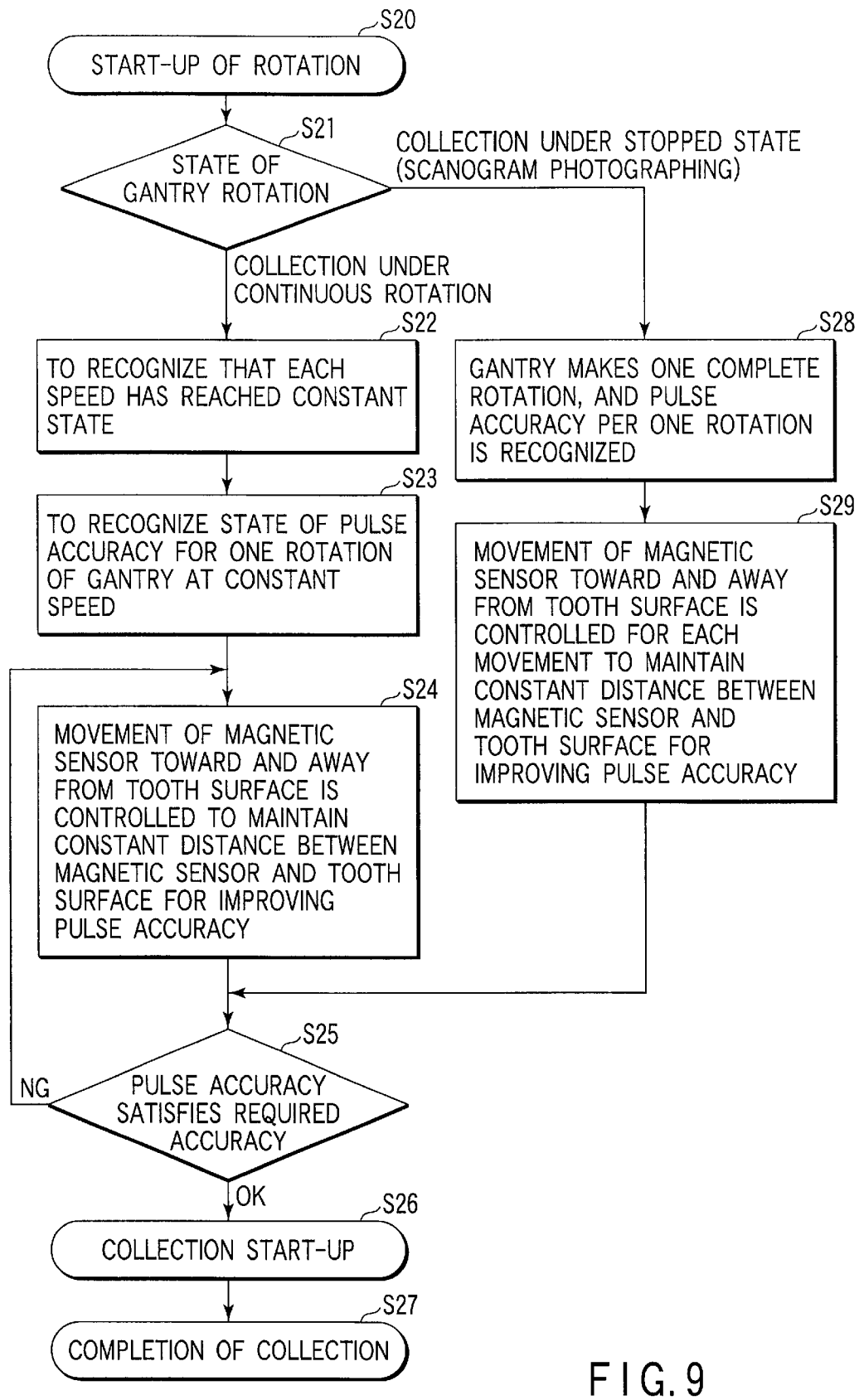
FIG. 9 is a flow chart for controlling the mechanism shown in FIG. 8 in the CT main control section shown in FIG. 2.

FIG. 9 shows the flow chart on the side of the CT main control in the case of performing the two control examples relating to the control to move the magnetic sensor 5 toward or away from the involute gear 10 in an X-ray CT apparatus. As shown in FIG. 9, rotation of the rotary section 1 is started in step S20 for starting the data collection for improving the pulse accuracy. In the tomograph mode in which the gantry is continuously rotated as shown in step S1, the operation proceeds to step S22, and in the scanogram mode in which the gantry is stopped at a predetermined position, the operation proceeds to step S23. To be more specific, in the tomograph mode, the gantry is continuously rotated in step S21. If the rotation of the gantry in step S22 reaches a predetermined speed that can be set, the rotation detecting pulse supplied to the correcting circuit 6 while the gantry maintained at the predetermined speed makes one complete rotation is monitored in step S23, and the accuracy of the pulse is detected in step S24. Information on the position in which the pulse accuracy fails to fall within a predetermined range is collected as shown in step S24, and the pulse accuracy in the case where the magnetic sensor 5 is moved toward or away from the involute gear 10 in this position is detected in step S24. Based on this detection, the control amount relating to the distance between the magnetic sensor 5 and the involute gear 10 in each rotating position is determined, and the clearance between the magnetic sensor 5 and the involute gear 10 is maintained at a predetermined distance in accordance with the control amount thus determined so as to control the driving mechanism of the magnetic sensor 5 such that the pulse accuracy falls within a predetermined range in any rotating position. The relationship between the rotating position and the control amount in respect of a predetermined rotating speed is collected in step S26 and stored in the memory device (not shown) of the CT main control section 9 so as to finish the data collection as shown in step S27. The collected data on the control amount are taken out when the rotating speed is determined, and the driving mechanism of the magnetic sensor 5 is controlled in accordance with the rotating speed. Also, it is desirable for the control amount for every rotating speed, which is stored in the memory device (not shown), to be periodically renewed in accordance with the rotating state of the apparatus.

In the scanogram mode, the gantry is driven to make one complete rotation so as to detect the pulse accuracy for every rotating position, as shown in step S23. Based on the detected pulse accuracy, the control amount relating to the distance between the magnetic sensor 5 and the involute gear 10 for every rotating position is determined as shown in step S28, and the driving mechanism of the magnetic sensor 5 is controlled based on the control amount such that the pulse accuracy falls within a predetermined range no matter where the X-ray tube may be positioned, as shown in step S25. The relationship between the position and the control amount is collected as shown in step S26 and stored in the memory device (not shown) of the CT main control section 9, thereby finishing a series of operations as shown in step S27.

The X-ray CT apparatus according to the second embodiment of the present invention described above produces the function and effect similar to those produced by the apparatus according to the first embodiment described previously and permits further improving and stabilizing the accuracy of the rotation detection.

THIRD EMBODIMENT

Figure 10A:
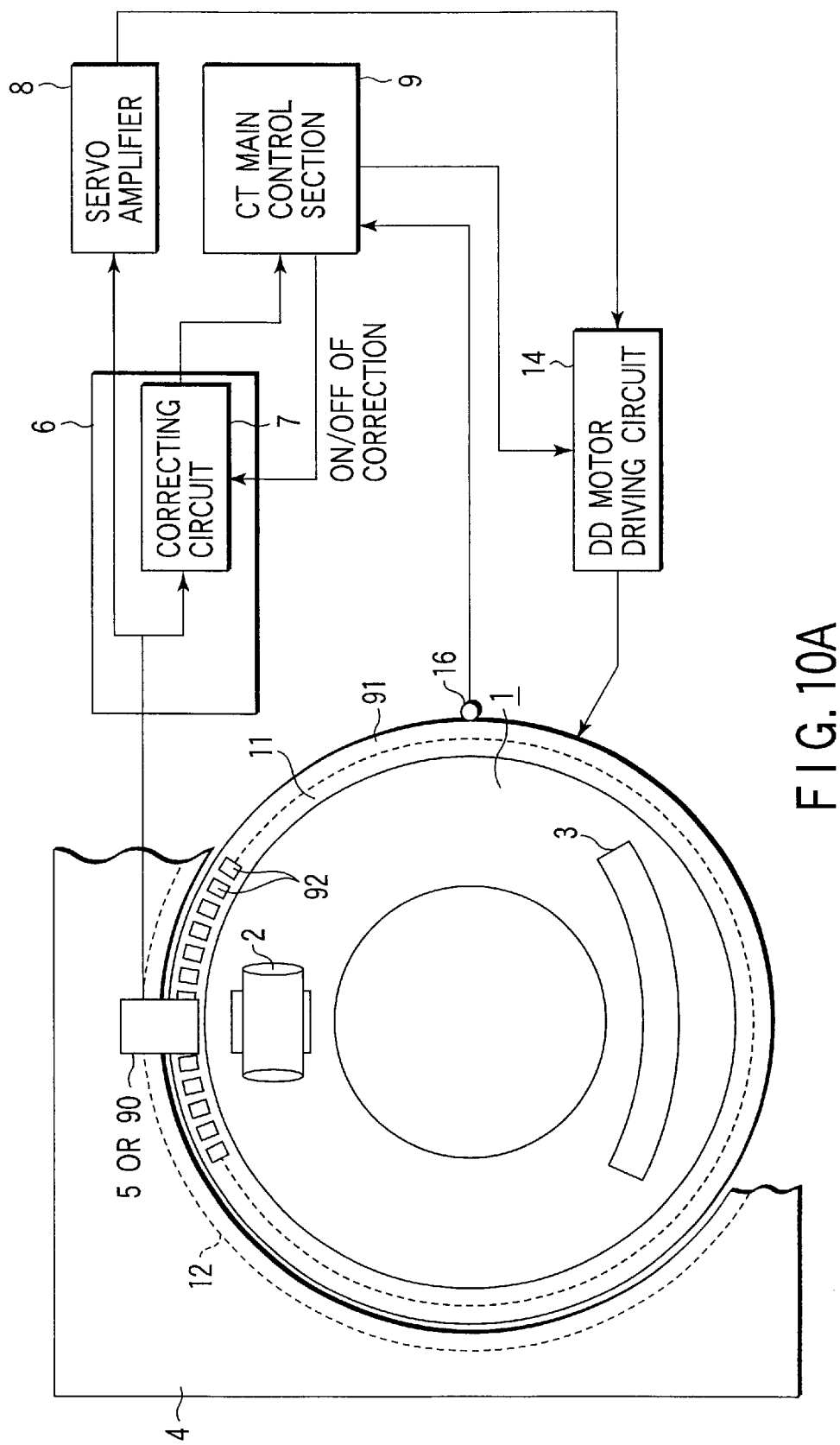
FIG. 10A is a block diagram showing an X-ray CT apparatus according to another embodiment of the present invention.

In an X-ray CT apparatus according to a third embodiment of the present invention, a slit disk 91 is mounted in place of the involute gear 10 to the rotary section 1, as shown in FIG. 10A. A periodic slit pattern 92 is formed in advance in the slit disk 91. Also, a transmission photo interrupter 90 or a magnetic reluctance sensor 5 is mounted to the stationary section 4 as a sensor for detecting the rotation of the rotary section 1 in a non-contact fashion by utilizing the slit of the slit disk 91, as shown in FIG. 10A.

The gantry of the X-ray CT apparatus has the construction of a direct drive (DD) motor driving system as in the first or second embodiment described previously. Incidentally, it is possible to employ the indirect driving system utilizing, for example, a belt in place of the DD motor driving system.

In the X-ray CT apparatus shown in FIG. 10A, the correcting circuit 7 for correcting the output signal generated from the transmission photo interrupter 90 or the magnetic reluctance sensor 5 by the zero-cross system is arranged as in the first embodiment described previously. The reference numerals common with FIGS. 10A and 2 denote the same members of the apparatus and, thus, the description thereof is omitted.

Figure 10B:
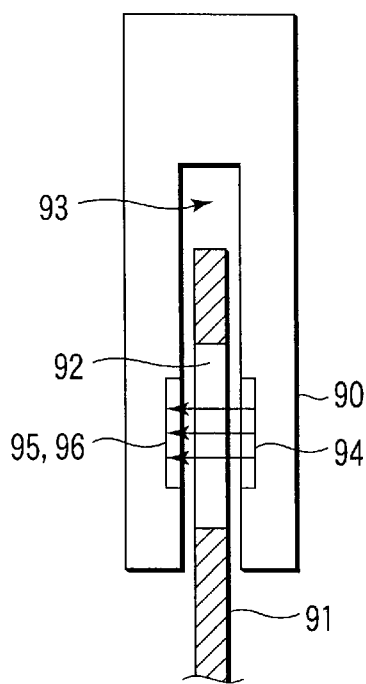
FIGS. 10B and 10C are cross sectional views each schematically showing the construction of the sensor shown in FIG. 10A.

FIG. 10B is a cross sectional view showing the transmission photo sensor 90 and the slit disk 91 as viewed laterally. As shown in FIG. 10B, the transmission photo interrupter 90 includes a clearance 93 as viewed laterally, and a light generating portion or a photo diode 94 is arranged to face a photo detector or photo sensors 95, 96 with the clearance 93 interposed therebetween. As shown in FIG. 10B, the transmission photo interrupter 90 is constructed such that the slit disk 91 mounted to the outer circumferential surface of the gantry rotary section 1 is arranged in a non-contact fashion in the clearance 93 of the transmission photo interrupter 90. The photo sensors 95, 96 are arranged in the rotating direction of the rotary section 1 such that each slit 92 of the slit disk 91 successively crosses the photo sensors 95, 96. The sine wave signal SA of phase A and the cosine wave signal SB of phase B as shown in FIG. 3B are generated from the two photo sensors 95, 96, and the zero-cross point of the sine wave signal SA of phase A and the cosine wave signal SB of phase B is detected by the zero-cross circuit within the correcting circuit 7 so as to generate pulse signals as shown in FIGS. 3C and 3D.

Figure 10C:
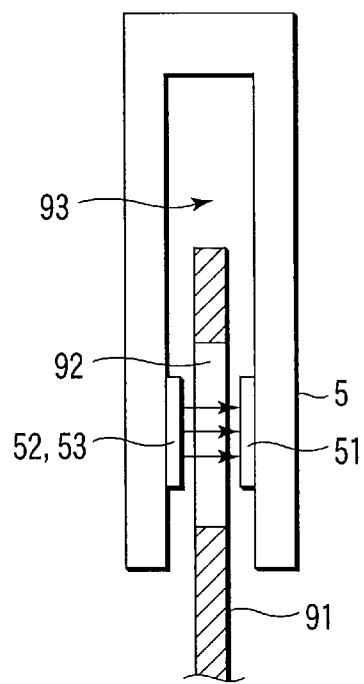

It is possible for the magnetic reluctance sensor 5 to be mounted to the slit disk 91 such that each slit 92 of the slit disk 91 successively crosses the magnetic reluctance elements 52 and 53 as shown in FIG. 3A. Alternatively, it is possible for the magnetic reluctance sensor 5 to be similar in construction to the photo interrupter 90 shown in FIG. 10B, as shown in FIG. 10C. It should be noted, however, that the slit disk 91 combined with the magnetic sensor is formed of a magnetic material having a permeability. In the sensor 5 shown in FIG. 10C, the magnet 5 is arranged to face the magnetic reluctance elements 52 and 52 with the clearance 93 interposed therebetween. In the magnetic sensor 5, the slit disk 91 mounted to the outer circumferential surface of the gantry rotary section 1 is arranged in a non-contact fashion within the clearance 93 of the sensor 5. The magnetic reluctance elements 52 and 53 are arranged in the rotating direction of the rotary section 1 such that each slit 92 of the slit disk 91 successively crosses over the magnetic reluctance elements 52 and 53. The sine wave signal SA of phase A and the cosine wave signal SB of phase B as shown in FIG. 3B are similarly generated from the magnetic reluctance elements 52 and 53, and the zero-cross point of the sine wave signal SA of phase A and the cosine wave signal SB of phase B is detected by he zero-cross circuit within the correcting circuit 7 so as to generate pulse signals as shown in FIGS. 3C and 3D.

In the combination of the transmission photo sensor 90 and the slit disk 91, if the slit disk 91 is rotated in accordance with rotation of the gantry rotary section 1, the light ray generated from the light generating section 94 passes through the slit disk 91 while the slit pattern 92 crosses the optical path of the light ray. It follows that a pulse is generated from the detecting section 95 to conform with the passage of the light ray through a single slit. Where, for example, 5400 slits are formed in the slit disk 91, 5400 pulse signals are generated by one complete rotation of the slit disk 91, and these pulse signals are multiplied by two by the multiplier circuit (not shown) so as to obtain 10,800 pulse signals. These pulse signals depend on the rotation of the gantry rotary section 1 and are supplied to the servo amplifier 8, the CT main control section 9, etc. so as to be utilized for detection of the rotating position, for the detection of the rotating speed, etc. of the gantry rotary section 1 as in the first embodiment.

Similarly, in the combination of the magnetic reluctance sensor 5 and the slit disk 91, the magnetic flux generated from the magnet 51 is guided into the magnetic reluctance elements 52, 53 when the slit 92 of the slit disk 91 is arranged between the magnet 51 and the magnetic reluctance elements 52, 53 so as to increase the resistance of these elements 52, 53. On the other hand, when the bridge between the adjacent slits 92 is arranged between the magnet 51 and the magnetic reluctance elements 52, 53, the magnetic flux generated from the magnet 51 is inhibited by the bridge between the adjacent slits 92 and, thus, is not guided to the magnetic reluctance elements 52, 53 so as to lower the resistance of these elements 52, 53. It follows that detection signal that are periodically changed as described previously with reference to FIGS. 3A and 3B are generated from the magnetic reluctance elements 52, 53 as the slits 92 of the slit disk 91 successively pass through the magnetic sensor 5.

The slit disk 91 shown in FIG. 10A is mounted to the outer circumferential surface of the gantry rotary section 1 and, thus, is sized large, making it difficult to prepare the slit disk 91 by a single metal plate. Therefore, the slit disk 91 is divided into a plurality of segments in the manufacturing step and, then, these segments are fixed to the gantry rotary section 1 so as to assemble the single slit disk 91. Where a single slit disk is assembled by combining a plurality of slit segments, it is certainly possible to manufacture the slit disk 91 relatively easily. However, the accuracy is lowered in the joining regions of the slit segments, with the result that it is possible for the pulse accuracy of the pulse signals that are formed on the basis of the output signals generated from the sensors 5, 90 to fail to fall within a predetermined allowable range, e.g., ±3% (or ±15% in terms of the pulse accuracy after the multiplying step).

Figure 11:
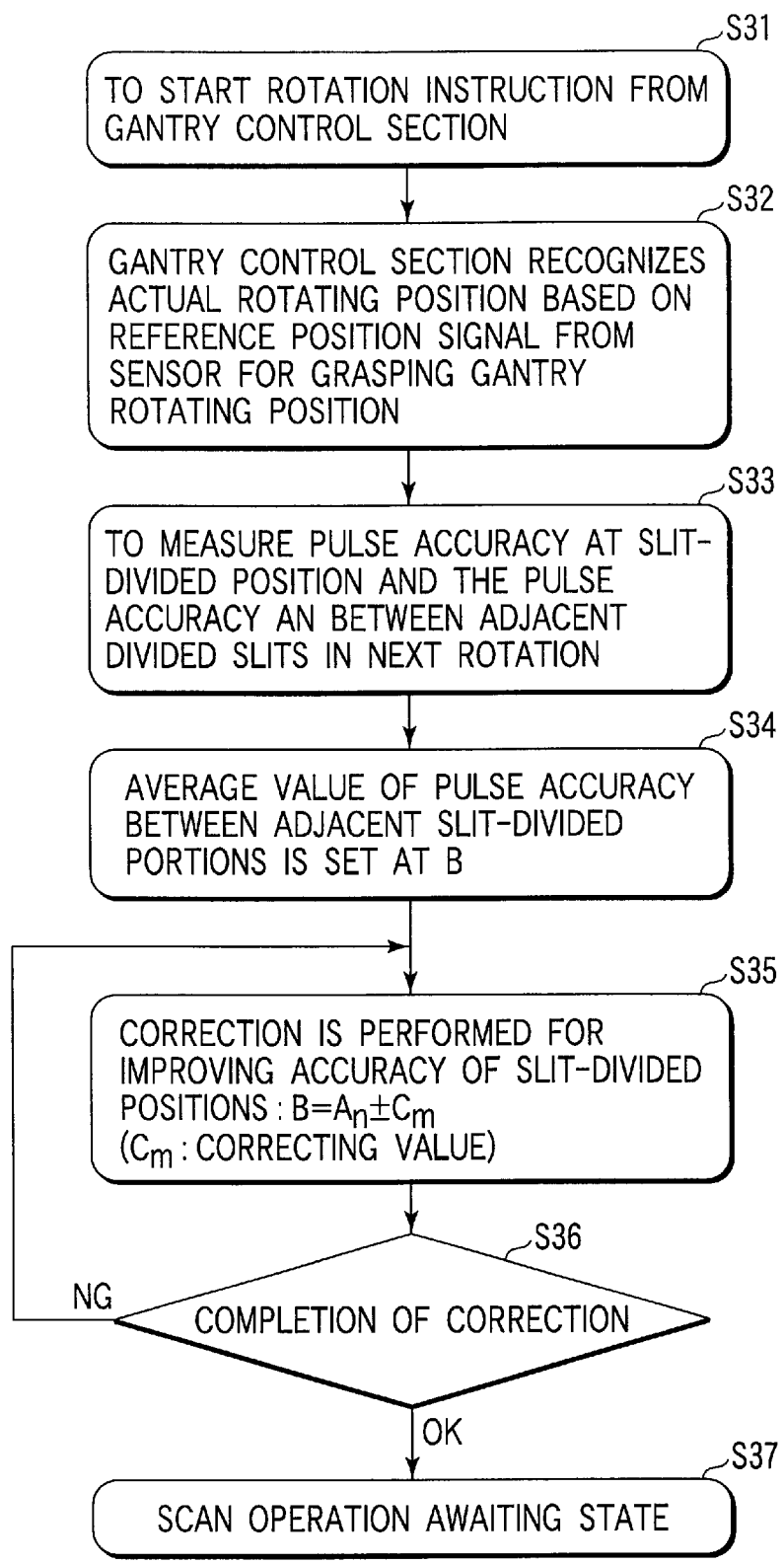
FIG. 11 is a flow chart showing the procedure to correct the output signal from the sensor shown in FIGS. 10B and 10C, which is executed by the CT main control section shown in FIG. 10A.

Under the circumstances, the correcting data are collected as shown in FIG. 11 so as to correct the output signals generated from the sensors 5, 90. To be more specific, the rotary support for rotating the rotary section is imparted from the gantry control section for controlling the gantry rotary section, which is included in the CT main control section, to the gantry rotating mechanism so as to start rotation of the gantry rotary section, as shown in step S31. In step S32, the reference position signal generated from the sensor 16 is supplied to the gantry rotary section, with the result that the rotating position of the gantry rotating section is recognized by the gantry control section. For example, it is recognized by the gantry control section that the X-ray tube 2 is positioned on the top position as shown in FIG. 10A, and the position of the X-ray tube 2 is recognized from the moving time of the X-ray tube 2 rotated at a constant speed from the time when the X-ray tube has passed through the top position. Since the slit disk 91 is divided into a plurality of segments and the connecting points of these segments are known in advance, the pulse PA when the connecting points have passed through the sensors 5, 90 is measured by the correcting circuit 6. Also, the pulse PB while the segments other than the connecting points pass through the sensors 5, 90 is measured at its positional relationship. The pulse accuracy An is obtained from the pulse PA at the connecting positions. Character "n" for the pulse accuracy An denotes the number of connecting points. For four segments, four pulse accuracy A1 to A4 are obtained for every connecting point. The pulse accuracy thus obtained is stored in the memory device (not shown). Also, the pulse accuracy is obtained from the pulse PB from the position between the adjacent connecting points, and an average B of the pulse accuracy of the pulse PB, which is dependent on the position between the adjacent connecting points, is obtained in step S34, and the average pulse accuracy B is stored in the memory device (not shown). In the next step, obtained is the correcting value Cn (Cn=B−An) for improving the pulse accuracy for every slit dividing position. If the correcting value Cn is obtained, the corresponding connecting point is detected in step S35, and the correcting value Cn is added to the pulse accuracy An every time the pulse corresponding to the connecting point is generated so as to correct the output pulse. If the correction is finished in step S36, the scanning operation for the next photographing is awaited.

Figure 12:
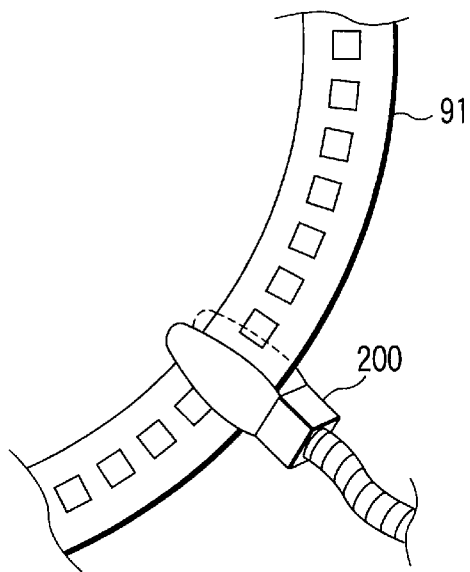
FIG. 12 is an oblique view schematically showing a suction duct that can be mounted in the magnetic slit of the X-ray CT apparatus shown in FIG. 10A.

Incidentally, in the rotation detection by the optical system shown in FIG. 10B, it is possible for the dust or the like to be attached to the slit pattern 92 of the slit disk 91 so as to shield the light generated from the transmission photo interrupter 90 and, thus, to lower the pulse accuracy. Under the circumstances, it is desirable in a more preferred embodiment to arrange a suction duct 200 as shown in FIG. 12 so as to impart the function of cleaning the slit to the apparatus. The suction duct 200 is arranged in a position to have the slit disk 91 held therein so as to operate in parallel to the rotation of the slit disk 91 (gantry rotary section 1), thereby sucking the dust attached to the entire circumferential surface of the slit pattern 92.

FOURTH EMBODIMENT

A fourth embodiment of the present invention relates to the non-contact type rotation detection using a simplified encoder.

The gantry of the X-ray CT apparatus employs the direct drive (DD) motor driving system like each of the first to third embodiments described above. Incidentally, it is possible to employ the indirect driving system in place of the DD motor driving system.

Figure 13:
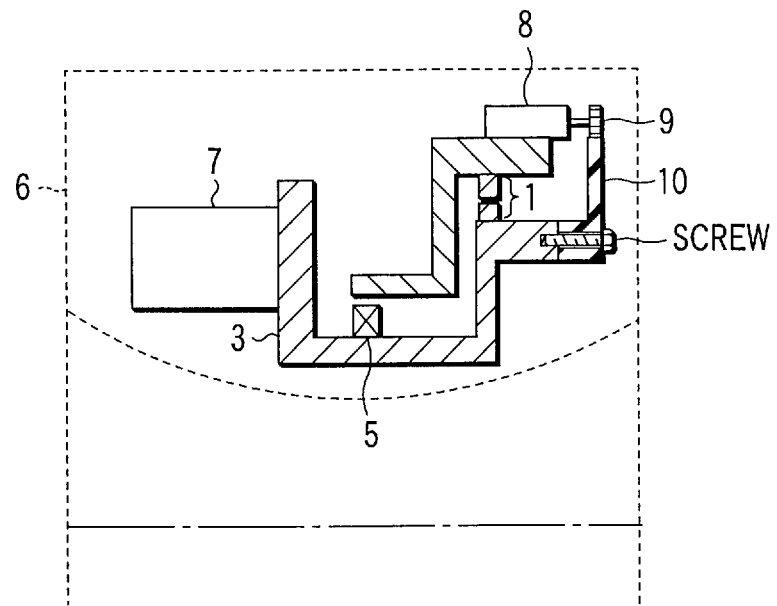
FIG. 13 is a cross sectional view schematically showing a first example of the internal construction of a gantry relating to the contact type rotation detection using a simplified encoder, which can be mounted to the X-ray CT apparatus shown in FIG. 10A.
Figure 14:
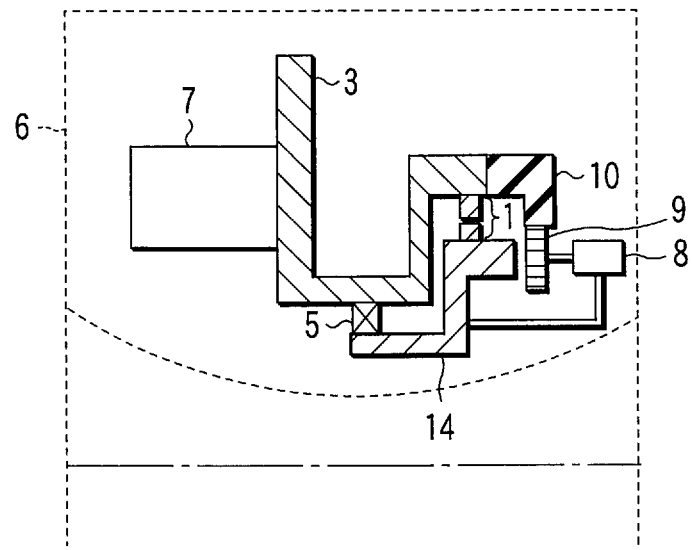
FIG. 14 is a cross sectional view schematically showing a second example of the internal construction of a gantry relating to the contact type rotation detection using a simplified encoder, which can be mounted to the X-ray CT apparatus shown in FIG. 10A.
Figure 15:
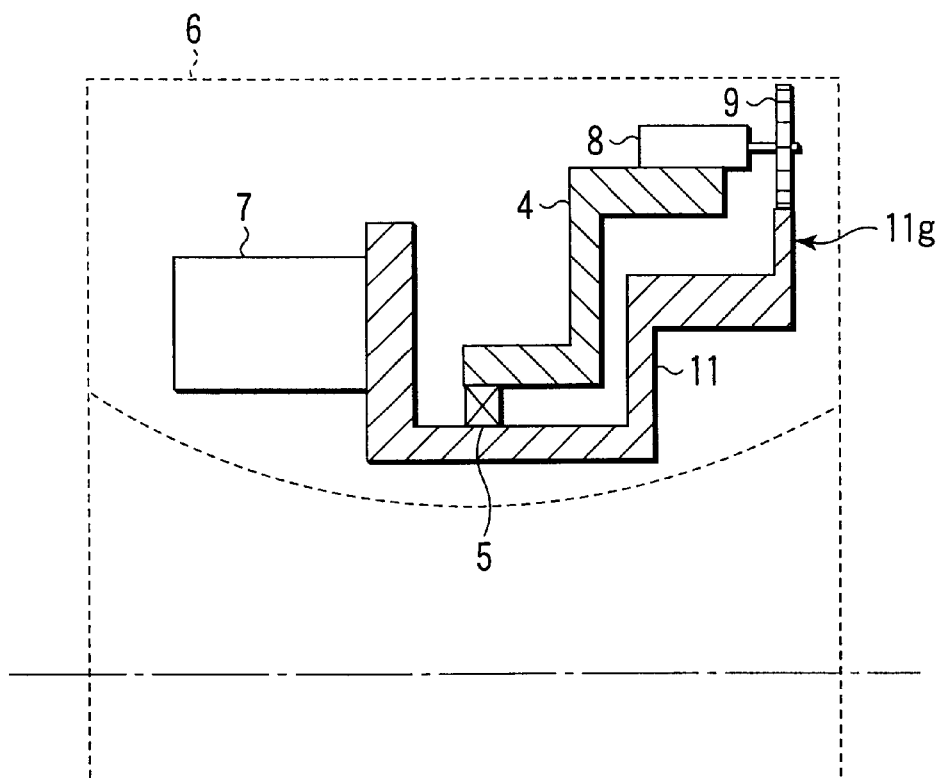
FIG. 15 is a cross sectional view schematically showing a third example of the internal construction of a gantry relating to the contact type rotation detection using a simplified encoder, which can be mounted to the X-ray CT apparatus shown in FIG. 10A.

FIGS. 13 to 15 are cross sectional views each showing the internal construction of the gantry relating to the non-contact type rotation detection using a simplified encoder according to the fourth embodiment of the present invention.

As shown in FIG. 13, a DD motor 1 consisting of a rotor and a stator is arranged between the gantry rotary section 3 and the gantry stationary section 4. The gantry rotary section 3 is supported rotatable relative to the gantry stationary section 4 via a bearing 5. As shown in FIG. 13, a rotary section gear 10 is mounted to the edge portion of the gantry rotary section 3 via a screw. The rotary section gear 10 is mounted coaxial with the cylindrical gantry rotary section 3 and can be detached easily from the gantry rotary section 3 by withdrawing the screw. A mounting unit 7 including an X-ray tube, an X-ray detector, etc. is mounted to the front side of the gantry rotary section 3. Also, for ensuring the safety, mounted is a cover 6 covering the structure of the rotary section 3 and the stationary section 4 of the gantry.

The gantry stationary section 4 includes a protruding portion, which is substantially S-shaped, for a satisfactory engagement with the concave portion of the gantry rotary section 3, and a bearing or the DD motor 1 is mounted to the protruding portion. The other construction of the gantry stationary section is omitted from the drawing. Also, a simplified encoder 8 for detecting the rotation is mounted to the outside (opposite to the rotary section) of the edge portion of the gantry stationary section 4. The simplified encoder 8, which is a general purpose encoder, is smaller than the resolver, high in reliability and cheap. The simplified encoder 8 has a rotary shaft, and a driven gear 9 meshing with the rotary section gear 10 is mounted to the rotary shaft. It is desirable for the driven gear 9 to be formed of a material slightly softer than the material of the rotary section gear 10 because, in this case, the relatively small driven gear 9, not the relatively large rotary section gear 10, is abraded first and, thus, it suffices to renew mainly the driven gear 9 alone.

In accordance with rotation of the gantry rotary section 3, the driven gear 9 is rotated and the rotary shaft of the simplified encoder 8, which is coaxial with the driven gear 9, is also rotated. As a result, the simplified encoder 8 generates pulse signals conforming with the rotation of the rotary shaft. The pulse signals thus generated are utilized for the detection of the rotating position and the for the detection of the rotating speed of the gantry rotary section 3.

FIG. 14 shows the construction of the outer wheel rotation, i.e., covers the case where the gantry rotary section 3 rotates along the outer circumferential surface relative to the gantry stationary section 4. As shown in FIG. 14, the simplified encoder 8 is mounted to the edge portion apart from the contact region between the gantry rotary section 3 and the gantry stationary section 4 and, thus, can be detached easily for the renewal.

FIG. 15 covers the case where a gear is formed in the gantry rotary section in the manufacturing process in place of attaching a rotary section gear formed as a separate member to the gantry rotary section. As shown in FIG. 15, a rotary section gear 11g meshing with the driven gear 9 is formed by, for example, the skiving in the edge portion of the gantry rotary section 11, i.e., the position facing the driven gear 9 of the simplified encoder 9.

The fourth embodiment described above is more advantageous in cost than the resolver system because the simplified encoder 8 is used in the fourth embodiment. It should also be noted that, if the simplified encoder 8 should be broken, the simplified encoder can be renewed easily by detaching the cover 6 and, thus, the maintenance can be performed easily.

The present invention is not limited to the first to fourth embodiments described above and can be worked in variously modified fashions.

As described above, the present invention provides an X-ray CT apparatus simple in construction, capable of maintenance with a low cost, and capable of the rotation detection or the rotation control with a high accuracy.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray CT apparatus, comprising:
a gantry including a substantially cylindrical rotary section and a stationary section rotatably holding the rotary section;
rotation detecting means for detecting the rotation of the rotary section to generate a rotation detecting signal;
correcting means for correcting the rotation detecting signal; and
calculating means for calculating at least one of the rotating position and the rotating speed of the rotary section on the basis of the corrected detecting signal from said correcting means.

2. The X-ray CT apparatus according to claim 1, wherein said correcting means detects the zero-cross of the rotation detecting signals to generate a detection pulse and includes a correcting circuit for correcting the detecting pulse with a reference clock signal.

3. The X-ray CT apparatus according to claim 1, further comprising a sensor for detecting the reference position of the rotary section to generate a reference position detecting signal, wherein
said control section includes an arithmetic calculating section for calculating the rotating position of said rotary section based on the reference position signal generated from said sensor and the rotating speed of said rotary section.

4. The X-ray CT apparatus according to claim 1, wherein said rotation detecting means includes a rotary slit plate fixed to said rotary section and rotated together with the rotary section, said rotary slit plate being divided into a plurality of sections in the rotating direction and including a connecting point positioned between the adjacent sections, and a sensor for detecting the rotation of the slit to generate a detecting signal.

5. The X-ray CT apparatus according to claim 4, further comprising a position sensor for detecting the reference position of the rotary section to generate a reference position detecting signal, wherein:
said calculating means includes an arithmetic section for calculating the rotating position of said rotary section based on the reference position signal generated from said position sensor and the rotating speed of said rotary section; and
said arithmetic section specifies the position of the connection portion of said slit plate, calculates the correcting value for correcting the rotation detecting signal generated from the specified position, and corrects the rotation detecting signal with the correcting value.

6. The X-ray CT apparatus according to claim 1, wherein said rotation detecting means includes:
a target section to be detected, which is mounted to any one of said rotary section and said stationary section to impart a periodic change in the magnetic flux in the circumferential direction of a circle coaxial with said rotary section; and
rotation detecting means mounted to the other of the rotary section and the stationary section for detecting the change in the magnetic flux that is generated in said target section in accordance with rotation of said rotary section to generate an electric signal conforming with said change in the magnetic flux.

7. The X-ray CT apparatus according to claim 6, wherein said target section is formed of a gear, and said rotation detecting means includes a magnetic flux generating means for generating a magnetic flux and a magneto-resistance element generating an electric signal showing a change in the resistance corresponding to the change in said magnetic flux receiving the function by the rotation of said gear.

8. The X-ray CT apparatus according to claim 7, wherein the tooth tip of said gear has a sharpened shape.

9. The X-ray CT apparatus according to claim 1, wherein said correcting means corrects the rotation detecting signal during rotation of said rotary section excluding the accelerating period and the decelerating period of the rotary section rotation.

10. An X-ray CT apparatus, comprising:
a gantry including a substantially cylindrical rotary section and a stationary section rotatably holding the rotary section;
rotation detecting means for detecting the rotation of the rotary section to generate a rotation detecting signal, said rotation detecting means including a target section to be detected, which is mounted to one of said rotary section and said stationary section to impart a periodic change in the magnetic flux in the rotating direction of the rotary section, and a rotation detecting sensor mounted to the other of the rotary section and the stationary section with a gap provided between said target section to detect the change in the magnetic flux generated in the target section in accordance with rotation of the rotary section and to generate a rotation detecting signal in accordance with detection of the change in the magnetic flux;
a sensor for detecting a reference position of the rotary section to generate a reference position detecting signal;
calculating means for calculating at least one of the rotating position and the rotating speed of the rotary section on the basis of said detection signal, said calculating means calculating the rotating position of the rotary section on the basis of the reference position signal generated from a position sensor and the rotating speed of the rotary section and also calculating a correction amount conforming with the position from said rotation detecting signal; and
moving means for slightly moving said rotation detecting sensor relative to said target section in accordance with said correcting amount to maintain constant the gap between the target section and the rotation detecting sensor.

11. The X-ray CT apparatus according to claim 10, wherein a correcting value is calculated based on the detecting signal obtained from said rotation detecting signal by rotating said target section to allow said target section to make at least one complete rotation, and the moving amount of said rotation detecting sensor is calculated on the basis of said correcting value.

12. The X-ray CT apparatus according to claim 10, wherein said calculating means calculates the moving amount conforming with the accuracy of said electric signal that is fluctuated by the rotating speed of said rotary section.

13. The X-ray CT apparatus according to claim 11, wherein said calculating means sets the scanogram photographing mode and rotates said rotary section to allow said rotary section to make at least one complete rotation for the photographing in the scanogram photographing mode.

14. An X-ray CT apparatus, comprising:
a gantry including a substantially cylindrical rotary section and a stationary section rotatably holding the rotary section;
rotation detecting means for detecting the rotation of the rotary section to generate a rotation detecting signal, said rotation detecting means including a ring-like target section to be detected, which is mounted to any one of said rotary section and said stationary section and having a periodic slit pattern formed therein, and an optical sensor mounted to the other of said rotary section and said stationary section in a manner to face said target section to detect the light ray passing through the slit pattern of the target section in accordance with rotation of the rotary section and, thus, to generate a detection signal;
correcting means for correcting the rotation detecting signal; and
calculating means for calculating at least one of the rotating position and the rotating speed of the rotary section on the basis of a corrected detecting signal from said correcting means.

15. The X-ray CT apparatus according to claim 14, wherein said optical sensor is a transmission photo interrupter.

16. The X-ray CT apparatus according to claim 14, further comprising means for removing dust attached to said slit pattern.

17. The X-ray CT apparatus according to claim 14, wherein said gantry includes a magnet mounted to said rotary section and a winding mounted to said stationary section, and said rotation calculating means includes rotation driving means for supplying an electric current to said winding.

18. An X-ray CT apparatus comprising:
a gantry including a substantially cylindrical rotary section and a stationary section rotatably holding the rotary section;
detectable means, mounted on one of the rotary section and the stationary section, for applying a periodical change on a magnetic flux generated in a circumferential space which is coaxially defined around said rotary section;
detecting means, mounted on the another of the rotary section and the stationary section, for detecting the change of the magnetic flux which is produced due to the rotation of the rotary section, to generate a rotation detecting signal; and
calculating means for calculating at least one of the rotating position and the rotating speed of the rotary section on the basis of the detecting signal from said detecting means,
wherein said detectable means includes a gear having tooth tips, and
wherein said detecting means includes means for applying the magnetic flux in the circumferential space, and a magneto-resistance element for producing a change in the resistance corresponding to the change in said magnetic flux to generate an electric signal.

19. The X-ray CT apparatus according to claim 18, wherein the tooth tip of said gear has a sharpened shape.

20. An X-ray CT apparatus comprising:
a gantry including a substantially cylindrical rotary section and a stationary section rotatably holding the rotary section;
motor for directly driving the rotary section to rotate the rotary section;
ring-shaped detectable section mounted on one of the rotary section and the stationary section and having a plurality of slits periodically arranged on said section;
detecting means, mounted on the another of the rotary section and the stationary section, for detecting light rays passing through the slit to generate a rotation detecting signal; and
means for generating an encoded signal based on the rotation detecting signal from said detecting means.

* * * * *